United States Patent [19]

Arai

[11] Patent Number: 5,215,716

[45] Date of Patent: Jun. 1, 1993

[54] INTEGRAL MULTILAYER ANALYTICAL ELEMENT

[75] Inventor: Fuminori Arai, Saitama, Japan

[73] Assignee: Fuji Photo Film Co., Ltd., Kanagawa, Japan

[21] Appl. No.: 667,001

[22] Filed: Mar. 11, 1991

Related U.S. Application Data

[63] Continuation of Ser. No. 291,047, Dec. 28, 1988, abandoned.

[30] Foreign Application Priority Data

Dec. 28, 1987 [JP] Japan .................. 62-330016

[51] Int. Cl.⁵ .................................. G01N 31/22
[52] U.S. Cl. ........................... 422/56; 422/57; 422/58; 436/170
[58] Field of Search ................. 422/56-58; 436/170

[56] References Cited

U.S. PATENT DOCUMENTS

| | | | |
|---|---|---|---|
| 4,292,272 | 9/1981 | Kitajima et al. | 422/56 |
| 4,363,874 | 12/1982 | Greenquist | 422/56 |
| 4,451,534 | 5/1984 | Akagi et al. | 428/372 |
| 4,478,942 | 10/1984 | Katsuyama et al. | 422/56 |
| 4,547,465 | 10/1985 | Eikenberry | 422/56 |
| 4,587,102 | 5/1986 | Nagatomo et al. | 422/56 |
| 4,594,224 | 6/1986 | Okaniwa et al. | 422/56 |
| 4,637,978 | 1/1987 | Dappen | 422/56 |
| 4,783,315 | 11/1988 | Arai et al. | 422/56 |
| 4,786,595 | 11/1988 | Arai et al. | 422/55 |
| 4,870,005 | 9/1989 | Akiyoshi et al. | 422/55 |

FOREIGN PATENT DOCUMENTS

| | | | |
|---|---|---|---|
| 0114403 | 12/1983 | European Pat. Off. | 33/52 |
| 0162302 | 4/1985 | European Pat. Off. | 33/52 |
| 2069132 | 1/1981 | United Kingdom | 33/48 |

OTHER PUBLICATIONS

Patent Abstracts of Japan, vol. 4, (1980), p. 46 C 31—K. K. Kuraray.

Primary Examiner—Jill A. Johnston
Attorney, Agent, or Firm—McAulay Fisher Nissen Goldberg & Kiel

[57] ABSTRACT

An integral multilayer analytical element comprising a reagent layer containing an indicator reagent composition capable of producing a detectable change corresponding to an analyte and a porous spreading layer composed of a fibrous fabric superposed on the reagent layer, wherein the yarn of said fabric comprises fibers having roughed surface, and an integral multilayer analytical element comprising a water-absorptive layer containing a hydrophilic polymer and a porous spreading layer composed of a fibrous fabric containing an indicator reagent composition capable of producing a detectable change corresponding to an analyte superposed on the water-absorptive layer, wherein the yarn of said fabric comprises fibers having roughed surface.

The rouging is carried out, for example, by alkali etching.

12 Claims, No Drawings

INTEGRAL MULTILAYER ANALYTICAL ELEMENT

This is a continuation of application Ser. No. 291,047, filed Dec. 28, 1988 and now abandoned.

BACKGROUND OF THE INVENTION

1. Field of the Invention

This invention relates to an integral multilayer analytical element for analysis of an analyte in an aqueous liquid sample. More particularly, this invention relates to an integral multilayer analytical element for analysis of an analyte in a liquid sample, such as a biological body fluid including blood (whole blood, blood plasma, blood serum), cerebrospinal fluid, lymph, saliva and urine, being dry-operative and useful for diagnosis in clinical field.

2. Description of the Prior Art

Integral multilayer analytical element is a form of dry-type analytical element being dry-operative and comprises a transparent support, a water-absorptive reagent layer containing a dye-forming reaction reagent and a hydrophilic polymer binder disposed thereon and a porous spreading layer disposed as the topmost layer. Various intergral multilayer analytical elements have been developed now.

The spreading layer has a metering action to spread an aqueous liquid sample spotted on the upper surface (the side far from the transparent support) thereof in lateral directions (the planar directions along the spreading layer) without uneven distribution of any component in the sample and to supply the sample to a water-absorptive reagent layer containing a hydrophilic polymer binder or a water absorption layer containing a hydrophilic polymer binder at a substantially fixed amount per unit area. The aqueous liquid sample includes biological body fluid, such as blood (whole blood, blood plasma, blood serum), lymph, saliva, cerebrospinal fluid, vaginal fluid or urine, drinking water, liquor, river water and industrial effluent. As the porous spreading layer, there are fibrous porous spreading layers, such as woven fabric spreading layers disclosed in U.S. Pat. No. 4,292,272 and GB 2,087,074A, knitted fabric spreading layers disclosed in EP 0,162,302A, the spreading layers composed of a paper containing fibrous pulp of an organic polymer disclosed in Japanese Patent KOKAI No. 57-148250 and the spreading layers formed by coating a suspension of fiber and hydrophilic polymer disclosed in U.S. Pat. No. 4,594,224, and nonfibrous porous spreading layers, such as membrane filter layers (blushed polymer layers) disclosed in U.S. Pat. No. 3,992,158 and continuous microspaces-containing isotropic porous layers (three dimensional lattice bead structure layer) where polymer particulates are joined so as to contact with each other at a point by using a polymer adhesive disclosed in U.S. Pat. No. 4,258,001.

Another form of dry-type analytical element being dry-operative is disclosed in DE 3,424,355A. The dry-type analytical element is a multilayer analytical element composed of a light-reflective or opaque support, a reagent layer containing a dye-forming reagent and a hydrophilic polymer binder to dissolve or solate by absorbing water and a porous registration layer disposed in this order. The porous registration layer may be composed of a similar material to the aforementioned spreading layer, and the spreading layer mentioned hereafter includes the porous registration layer unless other wise especially noted.

Among various spreading layers, woven fabric spreading layers and knitted fabric spreading layers (fabric spreading layer) can spread blood sample irrespective of whole blood, blood plasma or blood serum well, and they are excellent in the facility in the production of multilayer analytical element, the strength of the element and the like.

It is preferred that the spreading layer spreads the water in an aqueous liquid sample substantially without absorption, and therefore, the preferable fibers composing the fabric spreading layer are hydrophobic organic polymer fibers. However, in the multilayer analytical element where the fabric composed of hydrophobic organic polymer fiber is laminated onto a hydrophilic reagent layer through a thin gelatin binding layer like described in U.S. Pat. No. 4,292,272 or EP 0,162,302A, the adhesive strength of the spreading layer was insufficient. As a result, the spreading accuracy was inferior, and the analytical accuracy was insufficient.

In order to solve this problem, when the fabric was treated with glow discharge or corona discharge disclosed in GB 2,087,074A or glow discharge plasma treatment disclosed in Japanese Patent KOKOKU No. 59-11709, the adhesive strength was strengthened. As a result, the binding between the spreading layer and the reagent layer or the binding layer was made uniform, and the spreading accuracy was improved. However, another problem happened that undesirable interaction between a reagent component happened. That is, in the reagent layer in contact with the fabric spreading layer treated with glow discharge, corona discharge or plasma irradiation, when a diazonium salt was incorporated, the diazonium salt was decomposed, and the analytical accuracy became worse with the passage of storage time. While, when a tetrazolium salt was incorporated, the tetrazolium salt was reduced to produce a formazan dye. As a result, deviation of the analytical result occurred due to the irregular elevation of the base line of background, and the analytical accuracy became worse with the passage of storage time. Therefore, it was desired to develop a fabric spreading layer composed of a hydrophobic organic polymer fiber where the undesirable interaction between the reagent component and the degradation of the analytical accuracy with the storage time due to the interaction are removed, and the binding strength is sufficient.

SUMMARY OF THE INVENTION

An object of the invention is to provide an integral multilayer analytical element having an improved porous spreading layer composed of a fabric where the undesirable interaction between the fabrics of the spreading layer and a reagent composition causing the degradation of the reagent composition is low and nevertheless the binding force to a hydrophilic polymer binder is strong.

Another object of the invention is to provide an improved integral multilayer analytical element capable of determining an analyte in an aqueous liquid sample in a high accuracy by a simple dry process.

Another object of the invention is to provide an improved integral multilayer analytical element capable of determining an analyte in a blood sample including whole blood, blood plasma and blood serum in a high accuracy using an undiluted or low dilution ratio blood sample.

Another object of the invention is to provide an integral multilayer analytical element having a spreading layer capable of holding stably a component, particularly an enzyme, of a reagent composition, in the spreading layer containing a reagent composition containing an enzyme.

Another object of the invention is to provide an integral multilayer analytical element having an opaque fabric spreading layer capable of forming a white background.

Another object of the invention is to provide an integral multilayer analytical element hardly generating or discharging fiber waste and fiber dust through a continuous manufacturing process of the multilayer analytical element containing a lamination process of a long fabric strip of the spreading layer.

Another object of the invention is to provide a fabric spreading layer applicable to various forms of integral multilayer analytical element.

Such objects have been achieved by an integral multilayer analytical element comprising a reagent layer containing an indicator reagent composition capable of producing a detectable change corresponding to an analyte and a porous spreading layer composed of a fibrous fabric superposed on the reagent layer, wherein the yarn of said fabric comprises fibers having roughed surface.

The objects have also been achieved by an integral multilayer analytical element comprising a water-absorptive layer containing a hydrophilic polymer and a porous spreading layer composed of a fibrous fabric containing an indicator reagent composition capable of producing a detectable change corresponding to an analyte superposed on the water-absorptive layer, wherein the yarn of said fabric comprises fibers having roughed surface.

DETAILED DESCRIPTION OF THE INVENTION

The integral multilayer analytical element of the invention is characterized by the use of a fabric comprised of yarn(s) having roughed surface.

Since the multilayer analytical element of the invention has a spreading layer or porous registration layer composed of fabric, a support material is not essential. However, preferable embodiments are composed of a light-transmissive (transparent) water-impermeable support or a light-reflective or light-intransmissible (opaque) water-impermeable support, a reagent layer and a spreading layer superposed in this order, or the above-mentioned support, a water absorption layer and a reagent composition-containing spreading layer superposed in this order.

As the light-transmissive water-impermeable support, a known support employed in a usual multilayer analytical element may be employed. Such a support is a film, a sheet or a flat plate having a thickness of about 50 μm to about 1 mm, preferably about 80 μm to about 0.3 mm and capable of transmitting the object light, for example, having at least a partial region of a wave length in the range of about 200 nm to about 900 nm. Such a support may be made of a polyester (for example, polyethylene terephthalate or polycarbonate of bisphenol A), a cellulose ester (for example, cellulose diacetate, cellulose triacetate or cellulose acetate propionate), or polystyrene. Optical property of the support may be controlled by suspending a small amount of titanium dioxide particles, barium sulfate particles or the like. A known undercoating layer or a known binding layer may be provided on the surface of the support in order to secure the adhesion of the support to the reagent layer, a water-absorption layer or the like superposed on the support.

The light-reflective or light-intransmissible water-impermeable support includes the supports composed of the above light-transmissive water-impermeable support material containing a sufficient amount of titanium dioxide particles, barium sulfate particles or the like suspended therein for making the support opaque, paper immersed or coated with the above-mentioned polymer composing the transparent support, ceramic sheet, and opal glass. Preferable supports are the supports composed of the light-transmissive water-impermeable support material containing a sufficient amount of titanium dioxide particles, barium sulfate particles or the like. The thickness of the light-reflective or light-intransmissible water-impermeable support is also about 50 μm to about 1 mm, preferably about 80 μm to about 0.3 mm.

The multilayer analytical element of the invention may be provided with a water absorption layer or a registration layer containing a hydrophilic polymer between the support and the reagent layer containing a reagent composition described later or between the support and the porous spreading layer containing a reagent composition described later.

The water absorption layer is mainly composed of a hydrophilic polymer which absorbs water to swell, and it absorbs the water of aqueous liquid sample which reaches the surface of this layer. In the case of whole blood sample, it accelerates permeation of blood plasma component into the reagent layer. The water absorption layer preferably transmits the object light for detecting the detectable substance. The hydrophilic polymer used in the water absorption layer has a swelling ratio being in the range from about 150% to about 2,000%, preferably about 250% to about 1,500% at water absorption at 30° C. Examples of the hydrophilic polymer are gelatins including acid treated gelatin and deionized gelatin, gelatin delivatives such as phthalated gelatin and hydroxyalkyl acrylate grafted gelatin, agarose, pullulan, pullulan derivatives, polyacrylamide, polyvinyl alcohol and polyvinyl pyrrolidone. They are disclosed in EP 0,119,861A and EP 0,142,849A. The binary or ternary copolymers of methalyl alcohol disclosed in Japanese Patent KOKAI No. 62-32109 are also included. In general, gelatin, a gelatin derivative, polyacrylamide and polyvinyl alcohol are preferable. The dry thickness of the water-absorption layer is about 3 μm to about 100 μm, preferably about 5 μm to about 30 μm. The coating weight of the water-absorption layer itself is about 3 g/m$^2$ to about 100 g/m$^2$, preferably about 5 g/m$^2$ to about 30 g/m$^2$.

The registration layer can permeate the detectable substance produced in the reagent layer described later, and it can receive or trap the detectable substance. A radiation reflecting layer and/or light blocking layer may be provided between the registration layer and the reagent layer in order to detect the detectable substance by various radiation measuring techniques. The registration layer is transparent, and it can transmit the radiation for detecting the detectable substance. Moreover, the registration layer contains a hydrophilic polymer binder capable of swelling with the water in an aqueous liquid sample supplied at the time of analytical operation and a component capable of receiving or trapping the detectable substance and fixing it, in order to secure the permeability of the detectable substance and to receive or trap it. For example, in the case that the detectable substance is a dye, the fixing component to fix the detectable substance may be a mordant or a polymer mordant represented by image dye mordants used for gelatin silver halide color photographic photosensitive materials. The hydrophilic polymer binder may be selected from the aforementioned hydrophilic polymers for the water absorption layer. The thickness of the registration layer in dry state is in the range of about 3 $\mu$m to about 100 $\mu$m, preferably about 5 $\mu$m to about 30 $\mu$m, and in the coating amount, it is in the range of about 3 $g/m^2$ to about 100 $g/m^2$, preferably about 5 $g/m^2$ to about 30 $g/m^2$.

A pH buffer, base polymer or acid polymer described later may be incorporated into the water absorption layer and the registration layer in order to maintain the pH value in the element in a prescribed range at the time of conducting analytical operation.

The reagent layer is a water-absorptive or water-permeable layer where a reagent composition containing at least one kind of chemical component, biochemical component or immunochemical component capable of reacting with an analyte in an aqueous liquid sample to produce a detectable change is substantially uniformly dispersed, or a microporous water-permeable layer containing the above reagent composition. The detectable change means the change which can be detected mainly by an optical means, and for example, it is color change, coloration, emission of fluorescent light, variation of absorption wave length in ultraviolet region or generation of turbidity.

The reagent composition contained in the reagent layer is decided according to the analyte in an aqueous liquid sample and the biochemical reaction or chemical reaction selected for analyzing the analyte. When two or more reagent components participate in the selected reaction, the reagent components may be incorporated in one reagent layer or may be separated into two or more layers. The reagent composition includes various reagent compositions containing at least one kind of enzyme disclosed in the foregoing patent specifications or other known analytical reagent compositions or clinical assay reagent compositions.

As the examples of the reagent compositions containing at least one kind of enzyme, there are improved Trinder reagent compositions for the analysis of glucose containing glucose oxidase and peroxidase disclosed in U.S. Pat. No. 3,992,158, U.S. Pat. No. 4,292,272, U.S. Pat. No. 3,886,045, EP 0,103,901A, U.S. Pat. No. 4,098,574, EP 0,101,945A and EP 0,103,288A, etc., reagent compositions for the analysis of cholesterol containing cholesterol oxidase, peroxidase and, at need, cholesterol esterase disclosed in EP 0,122,641A, U.S. Pat. No. 3,983,005, Japanese Patent KOKAI Nos. 63-158000 and 63-258600, etc., reagent compositions for the analysis of urea nitrogen (BUN) containing urease disclosed in U.S. Pat. No. 4,066,403, U.S. Pat. No. 4,548,906 and Japanese Patent KOKAI No. 56-70460, etc., reagent compositions for the analysis of triglyceride or glycerol containing lipoprotein lipase, glycerol kinase, $\alpha$-glycerol-3-phosphate oxidase and peroxidase disclosed in GB 1,590,738, etc., reagent compositions for the analysis of bilirubin containing bilirubin-specific oxidase and peroxidase disclosed in U.S. Pat. No. 4,211,844 and EP 0,140,004A, etc., reagent compositions for the analysis of uric acid containing uricase (uric acid oxidase) and peroxidase disclosed in U.S. Pat. No. 4,089,747, EP 0,122,641A, etc., dye-forming reagent compositions for detecting hydrogen peroxide containing peroxidase disclosed in U.S. Pat. No. 4,269,938, Japanese Patent KOKAI No. 58-86457, etc., and the like.

As an example preferred to separate specific plural components in a dye-forming reagent composition from each other into two or more layers, there is a dye-forming reagent composition for measuring an enzyme-active or protein-bound low molecular weight analyte through a reduced form coenzyme containing an electron carrier, a dye precursor, an oxidized form coenzyme and an enzyme or an enzyme substrate capable of converting the above oxidized form coenzyme to the reduced form coenzyme, as major components. In this case, it is preferred to reparate the electron carrier from the dye precursor. The other components may be incorporated together with either of the above two components or into other layers. As the examples of the dye-forming reagent compositions containing an electron carrier, a dye precursor, an oxidized form coenzyme and an enzyme or an enzyme substrate capable of converting the above oxidized form coenzyme to the reduced form coenzyme, as major components, there are dye-forming reagent compositions for measuring lactate dehydrogenase activity disclosed in Clinica Chimica Acta, vol. 12, p 210 (1965) and DE 3,332,144A, dye-forming reagent compositions for measuring aspartate aminotransferase activity or alanine aminotransferase activity disclosed in Clinica Chimica Acta, vol. 28, p 431 (1970) and U.S. Pat. No. 4,024,021, DE 3,222,707A, DE 3,332,144A, dye-forming reagent compositions for measuring creatine kinase activity disclosed in Japanese Patent KOKOKU No. 46-9988, dye-forming reagent compositions for measuring creatine phosphokinase disclosed in U.S. Pat. No. 3,663,374 and DE 3,332,144A, dye-forming reagent compositions for measuring testosterone activity or androsterone activity, dye-forming reagent compositions for measuring amylase activity disclosed in GB 1,543,130, dye-forming reagent compositions for the analysis of glycerol disclosed in U.S. Pat. No. 3,992,158, dye-forming reagent compositions for the analysis of triglyceride disclosed in U.S. Pat. No. 4,001,089, GB 1,590,738, U.S. Pat. No. 4,273,870, and the like.

As the examples of the reagent compositions not containing enzyme, there are improved biuret reagent compositions for the quantitative analysis of total protein disclosed in U.S. Pat. No. 3,310,382, U.S. Pat. No. 4,132,528 Japanese Patent KOKAI Nos. 61-292063 and 59-51356, reagent compositions containing Bromophenol Blue for the quantitative analysis of albumin disclosed in Clinical Chemistry, vol. 15, pp 1006–1008 (1969), Clinica Chimica Acta, vol. 31, pp 87–96 (1971), Japanese Patent KOKAI No. 62-137564, etc., reagent compositions containing Arsenazo-III for the quantitative analysis of calcium disclosed in U.S. Pat. No. 4,166,093, reagent compositions containing o-Cresolphthalein Complexone for the quantitative analysis of calcium disclosed in Ed. Izumi Kanai and Masamitsu Kanai, "Rinsho Kensa-Ho Teiyo (The Elements of Clinical Assay Method)", 27th Edition, VII, pp 77–80 (Kanehara Shuppan, 1975), EP 0,254,202A, etc., reagent compositions containing a diazonium salt for the quantitative analysis of bilirubin disclosed in U.S. Pat. No. 4,548,905, EP 0,175,330A, and the like.

As the hydrophilic polymer used for the water-absorptive or water-permeable reagent layer, there are similar hydrophilic polymers used for the aforementioned water absorption layer. Preferable hydrophilic polymers for the reagent layer include gelatin, gelatin derivatives, polyacrylamide and polyvinyl alcohol. The thickness of the reagent layer containing a reagent composition in a hydrophilic polymer in dry state is in the range of about 5 μm to about 50 μm, preferably about 7 μm to about 30 μm, and in the coating amount, in the range of about 5 g/m² to about 50 g/m², preferably about 7 g/m² to about 30 g/m². The reagent layer is preferably substantially transparent.

The microporous water-permeable reagent layer is a microporous layer containing a reagent composition or a microporous structure composed of solid particulates and hydrophilic polymer containing a reagent composition. The microporous layer and the microporous structure include fibrous porous layers, such as fabric layers similar to the fabric spreading layers described later, the paper layers containing fibrous pulp of an organic polymer disclosed in Japanese Patent KOKAI No. 57-148250 and the porous layers formed by coating a suspension of fibers and hydrophilic polymer disclosed in U.S. Pat. No. 4,594,224, and nonfibrous isotropic porous layers, such as membrane filter layers (blushed polymer layers) and isotropic porous layers containing continuous microspaces where particulates such as polymer particulates are joined so as to contact with each other at a point by using a hydrophilic polymer binder disclosed in U.S. Pat. No. 3,992,158, and isotropic porous layers containing continuous microspaces where polymer particulates are joined so as to contact with each other at a point by using a polymer adhesive not swelling with water disclosed in U.S. Pat. No. 4,258,001 (three dimensional lattice structure layer). The layer thickness of the microporous reagent layer in dry state is in the range of about 7 μm to about 250 μm, preferably about 10 μm to about 250 μm. In the case of superposing the fabric layer on the microporous reagent layer, both layers are preferably joined by a porous binding layer disclosed in EP 0,166,365A and EP 0,226,465A.

As an embodiment of the invention, the multilayer analytical element is comprised of the fabric spreading layer containing the aforementioned reagent composition and the water absorption layer or the registration layer disposed thereunder, if necessary, through a binding layer. As another embodiment of the invention, the multilayer analytical element is comprised of the reagent layer formed by using a polymer capable of dissolving or solating with the solvent of an aqueous liquid sample, such as polyvinyl alcohol, polyvinylpyrrolidone, carboxymethyl cellulose, sodium alginate, uncured gelatin or agar, as the polymer binder of the reagent layer, and a fabric directly laminated thereon as the porous registration layer.

Every type of the reagent layer may contain a pH buffer, a known acid polymer or base polymer described later in order to maintain the pH at the time of analytical operation.

The multilayer analytical element of the invention preferably contains a known pH buffer capable of maintaining a prescribed value in the range of about pH 2 to about pH 12 through the analytical operation by spotting an aqueous liquid sample. The pH buffer may be incorporated into at least one layer of the porous spreading layer, the reagent layer, the water absorption layer or the binding layer described later, and the reagent layer and/or the water absorption layer are preferred. The pH buffers suitable for integral multilayer analytical elements are described in "Kagaku Benran Kiso-Hen" pp 1312–1320 (Maruzen, Tokyo, 1966), R. M. C. Dawson et al, "Data for Biochemical Research", 2nd Ed., pp 476–508 (Oxford at the Clarendon Press, 1969), "Biochemistry", vol. 104, pp 300–310 (1980). The pH buffer includes buffers containing tris(hydroxymethyl)aminomethane, buffers containing a phosphate, buffers containing a borate, buffers containing a carbonate, buffers containing glycine and the like. Examples are N,N-bis(2-hydroxyethyl)glycine (Bicine), sodium or potassium salt of N-2-hydroxyethylpiperazine-N'-2-hydroxypropane-3-sulfonic acid (HEPPS), sodium or potassium salt of β-hydroxy-4-2-hydroxyethyl-1-piperazinepropanesulfonic acid (HEPPSO), sodium or potassium salt of 3-(cyclohexylamino)-1-propanesulfonic acid (CAPS), sodium or potassium salt of N-[tris(-hydroxymethyl)methyl]-3-aminopropanesulfonic acid (TAPS), sodium or potassium salt of N-2-hydroxyethylpiperazine-N'-2-ethanesulfonic acid (HEPES) and a combination of any of them and an acid, an alkali or a salt.

The hydrophilic polymer used for the water absorption layer, the registration layer, the reagent layer or the like may be an intermediate layer suitably cured by using a crosslinking agent. The crosslinking agent includes known vinylsulfone crosslinking agents, such as 1,2-bis(vinylsulfonylacetamide)ethane and bis(vinylsulfonylmethyl) ether, and aldehydes for gelatin and aldehydes and epoxy compounds containing two glycidyl groups for methallyl alcohol copolymers.

A known binding layer composed of a similar hydrophilic polymer used for the water absorption layer, such as deionized gelatin or polyvinyl alcohol may be provided on the reagent layer for the purpose of binding the spreading layer securely. The thickness of the binding layer in dry state is in the range of about 0.5 μm to about 5 μm.

The multilayer analytical element of the invention is characterized by the fabric spreading layer composed of the yarn containing the fibers having roughed surface. The roughness is formed at least on the exposed surface of the fibers positioned on one of both faces of the fabric. The difference of elevation (depth) of the roughness in the direction perpendicular to the fiber axis is about 0.05 μm to about 3 μm, preferably about 0.2 μm to about 0.7 μm, and the density of the roughness (e.g. aggregation of micro concavities) is about 1 to about 200/μm². The surfaces of entire fibers composing the fabric may be roughed with the above roughness. Moreover, the above roughed portion may be further roughed with fine roughness having about 50 nm to about 200 nm in depth. The roughness may be formed by a known method, such as alkali etching by heating organic polymer fibers or knitted or woven fabric made thereof in an aqueous alkali solution or alkali etching by heating organic polymer fibers containing particulates such as silica sol or titanium dioxide or knitted or woven fabric made thereof disclosed in Japanese Patent KOKOKU No. 59-24233.

The woven fabric may be selected from the woven fabrics having various structures; however plain weave fabrics, such as broad cloth and poplin, are preferable. The yarn composing the woven fabric may be irrespective of filament twist yarn (long fiber yarn), filament untwisted yarn or spun yarn. The thickness of the yarn is in the range of about 20 S to about 150 S, preferably about 40 S to about 120 S represented by cotton yarn number, and about 35 D to about 300 D, preferably about 45 D to about 130 D represented by silk denier. The thickness of the woven fabric is in the range of about 50 µm to about 500 µm, preferably about 120 µm to about 350 µm, and the void content of the woven fabric is in the range of about 40% to about 90%, preferably about 50% to about 85%.

The knitted fabric may be selected from the knitted fabrics having various structures, and warp-knitted fabrics and weft-knitted fabrics are preferable. The warp-knitted fabrics include single atlas stitch fabrics, tricot fabrics, double tricot fabrics, milanese fabrics, raschel fabrics, and the like, and the weft-knitted fabrics include plain stitch fabrics, pearl stitch fabrics, rib stitch fabrics and interlock stitch fabrics. Preferable knitted fabrics include tricot fabrics, double tricot fabrics, raschel fabrics, milanese fabrics and interlock stitch fabrics. The yarn composing the knitted fabric may be irrespective of filament twist yarn (long fiber yarn), filament untwisted yarn or spun yarn. The thickness of the yarn is in the range of about 40 S to about 150 S, preferably about 60 S to about 120 S represented by cotton yarn number, and about 35 D to about 130 D, preferably about 45 D to about 90 D represented by silk denier. The gauge number in the knitting process of the knitted fabric is in the range of about 20 to about 50. The thickness of the knitted fabric is in the range of about 100 µm to about 600 µm, preferably about 150 µm to about 400 µm, and the void content of the knitted fabric is in the range of about 40% to about 90%, preferably about 50% to about 85%.

The yarn composing the woven fabric or the knitted fabric may be composed of regenerated cellulose fiber, fibers of semisynthetic organic polymer, such as cellulose diacetate or cellulose triacetate, fibers of synthetic organic polymer, such as polyamides, acetalized polyvinyl alcohol or polyethylene terephthalate, or mixed fibers of regenerated cellulose, semisynthetic organic polymer or synthetic organic polymer and natural fibers, such as cotton, silk or wool. Polyethylene terephthalate fibers are preferred.

After alkali etching treatment, the yarn or the fabric of which fibers are roughed is preferably washed with water to remove the alkali residues sufficiently. The oils and fats supplied or adhered during manufacturing yarn or fabric are substantially removed by a degrease treatment, such as washing with water. Moreover, the fabric may be treated with a surfactant solution, preferably an aqueous nonionic surfactant solution by immersing, coating or spraying disclosed in U.S. Pat. No. 4,292,272, GB 2,087,074A and Japanese Patent KOKAI No. 57-148250, etc., an aqueous hydrophilic polymer solution by immersing, coating or spraying disclosed in EP 0,254,202A, an aqueous solution of a hydrophilic cellulose derivative and a nonionic surfactant having an HLB value of more than 10 by immersing, coating or spraying disclosed in EP 0,162,301A, or a combination of two or more of the above treatments. By the above treatment, binding to the underside layer can be strengthened, and metering action or the metering action corresponding to hematocrit value can be controlled.

As the method of incorporating a pH buffer composition into a layer on the underside of the spreading layer and a hydrophilic polymer and a nonionic surfactant together with the reagent composition into the porous spreading layer, there is the following method. A layer containing the pH buffer composition is provided by coating an aqueous solution containing the pH buffer composition and a hydrophilic polymer binder, followed by drying, and then the spreading layer is laminated. The hydrophilic polymer and the nonionic surfactant are dissolved or suspended in an organic solvent, such as ethanol, propanol, butanol or isopropanol, together with the reagent composition, and coated or sprayed onto the spreading layer to be incorporated therein, and dried.

A surfactant, preferably a nonionic surfactant, may be incorporated into the spreading layer, the reagent layer, the water absorption layer, the registration layer, the binding layer, or the like. As the examples of the nonionic surfactant, there are p-octylphenoxypolyethoxyethanol, p-nonylphenoxypolyethoxyethanol, p-nonylphenoxypolyglycidol, polyoxyethylene oleyl ether, polyoxyethylene sorbitan monolaurate, octylglucoside, and the like. By incorporating a nonionic surfactant into the reagent layer, the water absorption layer or the registration layer, this layer easily absorb the water in an aqueous liquid sample substantially uniformly at the time of analytical operation, and the liquid contact with the spreading layer becomes rapid and substantially uniform. While, by incorporating a nonionic surfactant into the spreading layer, the metering action to the aqueous liquid sample is improved. A suitable content of the nonionic surfactant in the spreading layer is in the range of about 100 mg to about 3 g, preferably about 200 mg to about 2 g, per 1 $m^2$ of the spreading layer.

The integral multilayer analytical element of the invention may be prepared according to a known method described in the foregoing patent specifications.

The integral multilayer analytical element of the invention is preferably cut into square pieces having a side of about 15 mm to about 30 mm or circular pieces having a similar size, and put in a slide frame disclosed in U.S. Pat. No. 4,169,751, Japanese Patent KOKAI No. 57-63452, U.S. Pat. No. 4,387,990 and Japanese Utility Model KOKAI No. 58-32350, U.S. Pat. No. 4,169,751, U.S. Pat. No. 4,387,990, PCT application WO 83/00391, etc. to use. While, it may be made strip-shaped, and placed in a cassette or a magazine. Besides, it may be made small piece-shaped, and adhered to or placed in a card having an opening.

In the case of the multilayer analytical element composed of the light-reflective or opaque support, the reagent layer containing the reagent composition and the hydrophilic polymer binder to absorb water to dissolve or solate and the porous registration layer laminated in this order, it is preferable to use the support having a size greater than the reagent layer and the porous registration layer, or to fix the support onto a slender holder combined with a handle, like described in DE 3,424,355A.

The measurement is carried out, for example, according to the manner disclosed in the specifications of the foregoing patents. About 5 µl to about 30 µl, preferably about 8 µl to about 15 µl of an aqueous sample is spotted on the spreading layer, and incubated at a definite temperature in the range of about 20° C. to about 40° C., preferably around 37° C., for 1 to 10 minutes. Thereafter, using a light having wave lengths of maximum absorption or its vicinity in visible region, color change or coloring in the multilayer analytical element is measured from the side of the transparent support through reflection photometry, and the analyte in the sample is determined using a calibration curve previously obtained and according to the principle of colorimetry.

The quantitative analysis of the analyte can be conducted in a high accuracy by fixing the spotted amount of the sample, incubation time and temperature. In the case of using the light-reflective or opaque support, the color change or coloring in the element is measured from the side of the spreading layer or the porous registration layer through reflection photometry. When this measurement is carried out by using the chemical-analytical apparatus disclosed in Japanese Patent KOKAI Nos. 60-125543, 60-220862, 61-294367 and U.S. Pat. No. 4,424,191, highly accurate results can easily be obtained by a simple operation.

EXAMPLES

Example 1

The following two kinds of fabrics were prepared from the polyethylene terephthalate (PET) fibers containing silica sol having a particle size in the range of about 10 nm to about 20 nm produced according to the method described in Japanese Patent KOKOKU No. 59-24233.

Plain weave fabric made of PET filament yarn corresponding to 50 deniers having a thickness of about 140 $\mu$m.

Interlock knitted fabric made of PET filament yarn corresponding to 50 deniers knitted by 40 gauges having a thickness of about 250 $\mu$m.

The above two kinds of the fabrics were immersed in 4% sodium hydroxide aqueous solution, and alkali etching was conducted at 95° C. for 20 minutes. Subsequently, the fabrics were sufficiently washed with water and sodium hydroxide was removed. After drying, the weight of the fabrics was measured, and the reduced weight of each fabric was about 10%. When the dried fabrics were observed by a microscope, the surface of the fibers of the filament yarns were roughed, and the depth between the top and the bottom was in the range of about 0.3 $\mu$m to about 0.5 $\mu$m.

Example 2

A water absorption layer was provided on a colorless transparent PET film (support) 180 $\mu$m in thickness by coating the following aqueous gelatin solution so as to become the following amount, and dried. Subsequently, it was allowed to stand at 45° C. for 3 days to cure the water absorption layer.

| | |
|---|---|
| Deionized gelatin | 27 g/m$^2$ |
| Nonylphenoxypolyethoxyethanol | 260 mg/m$^2$ |
| (Containing 10 hydroxyethylene units on average) | |
| 1,2-Bis(vinylsulfonylacetamido)ethane | 130 mg/m$^2$ |

On the cured water absorption layer, the following aqueous gelatin solution was coated so as to become the following amount, and dried to form a binding layer.

| | |
|---|---|
| Deionized gelatin | 4.0 g/m$^2$ |
| Nonylphenoxypolyethoxyethanol | 8 mg/m$^2$ |
| (Containing 10 hydroxyethylene units on average) | |

The binding layer was uniformly moistened with water, and the roughed plain weave fabric obtained in Example 1 was lightly pressed to laminated thereon as the spreading layer to obtain an integral multilayer analytical element not containing the reagent composition.

Comparative Example 1A

An integral multilayer analytical element according to the prior art was prepared in the same manner as Example 2, except that the plain weave fabric did not contain the silica sol and was not roughed.

Comparative Example 1B

An integral multilayer analytical element according to the prior art was prepared in the same manner as Example 2, except that the plain weave fabric did not contain the silica sol and that the plain weave fabric was not treated with alkali etching but treated with glow discharge under the conditions of electric energy of 1.6 kW/m$^2$ and oxygen concentration of 0.1 Torr for about 30 sec.

Properties Evaluation Test 1

The above three kinds of the multilayer analytical elements were cut into strips 15 mm in width, and the force necessary to separate the spreading layer from the binding layer at 180 degrees was measured, and the following results were obtained.

| | Force for Separation |
|---|---|
| Example 2 | 89 g |
| Comparative 1A | 5 g |
| Comparative 1B | 120 g |

In the above results, the adhesive strength of the multilayer analytical element of the invention is suitable as well as Comparative Example 1B.

Properties Evaluation Test 2

3,3'-(3,3'-dimethoxy-4,4'-biphenylene)bis[2,5-bis(p-nitrophenyl)-2H-tetrazolium] chloride 1.0 w/v methanol solution was prepared, and coated to the spreading layer of each element at the rate of 200 ml/m$^2$, and dried at 50° C. For 15 minutes. The optical density of the color (background) of the element was measured using a visible light having a central wave length of 540 nm from the PET support side by reflection photometry, and the following results were obtained.

| | Reflection Optical Density |
|---|---|
| Example 2 | 0.182 |
| Comparative 1A | 0.185 |
| Comparative 1B | 0.592 |

In the above results, the coloring of the tetrazolium salt to increase background color is little in the case of the element of the invention as well as Comparative Example 1A.

Properties Evaluation Test 3

The following aqueous diazonium salt solution was prepared.

| | |
|---|---|
| p-Sulfobenzenediazonium p-toluenesulfonic acid salt | 4.0 g |
| Sulfosalicylic acid | 4.0 g |
| Water | 100 mg |

This aqueous solution was coated to the spreading layer of each element at the rate of 180 ml/m$^2$, and dried at 35° C. for 60 minutes. Subsequently, each one square piece having a size of 15 mm × 15 mm of the multilayer analytical element containing the diazonium salt in the spreading layer was immersed in 5 ml of water at room temperature (about 25° C) for about 5 minutes, and most of the diazonium salt not sufficiently adsorbed on the spreading layer was eluted out. After the multilayer analytical element was taken out, the diazonium salt remaining in the water was colored by adding 5.0% chromotropic acid aqueous solution. The content of the diazonium salt was measured colorimetrically, and the remaining amount of the diazonium salt in the spreading layer was decided by substracting the amount of the diazonium salt in the water from the initial amount contained in the spreading layer. The remaining rates of the diazonium salt in the spreading layer thus obtained are described in the following table.

|  | Remaining Rate |
| --- | --- |
| Example 2 | 98% |
| Comparative 1A | 97% |
| Comparative 1B | 72% |

The above results indicate that the absorption force of the diazonium salt in the spreading layer of the element of the invention is great as well as Comparative Example 1A.

In the sum of the results of the above evaluation tests, the spreading layer of the integral multilayer analytical element of the invention is bound to the binding layer with a suitable strength, and it can securely hold the tetrazolium salt and the diazonium salt without decomposing them.

Example 3

An integral multilayer analytical element not containing the reagent composition was prepared in the same manner as Example 2, except that the roughed interlock knitted fabric obtained in Example 1 was used instead of the roughed plain weave fabric.

Comparative Example 2A

An integral multilayer analytical element according to the prior art was prepared in the same manner as Example 3, except that the interlock knitted fabric did not contain the silica sol and was not roughed.

Comparative Example 2B an integral multilayer analytical element according to the prior art was prepared in the same manner as Example 3, except that the interlock knitted fabric did not contain the silica sol and that the interlock knitted fabric was not treated with alkali etching but treated with glow discharge under the conditions of electric energy of 1.6 kW/m$^2$ and oxygen concentration of 0.1 Torr for about 30 sec.

Similar properties evaluation tests to Example 2 were carried out, and similar results were obtained.

Example 4

A water absorption layer was provided on a colorless transparent PET film (support) 180 um in thickness by coating the following aqueous gelatin solution so as to become the following content, and dried.

| Deionized gelatin | 20 g/m$^2$ |
| --- | --- |
| Nonylphenoxypolyethoxyethanol | 200 mg/m$^2$ |
| (Containing 10 hydroxyethylene units on average) | |

The water absorption layer was uniformly moistened with water, and the roughed interlock knitted fabric obtained in Example 1 was lightly pressed to laminate thereon as the spreading layer.

The following diazonium salt aqueous solution was prepared.

| p-Sulfobenzene diazonium p-toluenesulfonate | 4.0 g |
| --- | --- |
| Diphylline | 150 g |
| (CAS Registry N2[479-18-5]) | |
| Poly(2-acrylamide-2-methylpropanesulfonic acid) | 10 g |

The above aqueous solution was coated to the above spreading layer at a rate of 100 ml/m$^2$, and dried at 35° C. for 60 minutes to obtain an integral multilayer analytical element for the quantitative analysis of bilirubin containing the diazonium salt-containing reagent composition in the spreading layer.

Comparative Example 3A

An integral multilayer analytical element according to the prior art was prepared in the same manner as Example 4, except that the interlock knitted fabric did not contain the silica sol and was not roughed.

Comparative Example 3B

An integral multilayer analytical element according to the prior art was prepared in the same manner as Example 4, except that the interlock knitted fabric did not contain the silica sol and that the interlock knitted fabric was not treated with alkali etching but treated with glow discharge under the conditions of electric energy of 1.6 kW/m$^2$ and oxygen concentration of 0.1 Torr for about 30 sec.

Comparative Example 3C

An integral multilayer analytical element according to the prior art was prepared in the same manner as Example 4, except that the interlock knitted fabric was not treated with alkali etching but treated with glow discharge under the conditions of electric energy of 1.6 kW/m$^2$ and oxygen concentration of 0.1 Torr for about 30 sec.

Properties Evaluation Test 1

The above four kinds of the multilayer analytical elements were cut into strips 15 mm in width, and the force necessary to separate the spreading layer from the binding layer at 180 degrees was measured, and the following results were obtained.

|  | Force for Separation |
| --- | --- |
| Example 4 | 158 g |
| Comparative 3A | 22 g |
| Comparative 3B | 155 g |
| Comparative 3C | 180 g |

In the above results, the adhesive strength of the multilayer analytical element of the invention is suitable as well as Comparative Examples 3B and 3C.

Properties Evaluation Test 2

The optical density of the color (background) of each element was measured using a visible light having a central wave length of 540 nm from the PET support side by reflection photometry, and the following results were obtained.

|  | Reflection Optical Density |
|---|---|
| Example 4 | 0.182 |
| Comparative 3A | 0.181 |
| Comparative 3B | 0.528 |
| Comparative 3C | 0.540 |

In the above results, the coloring of the diazonium salt to increase background color is little in the case of the element of the invention as well as Comparative Example 3A.

Properties Evaluation Test 3

Each 10 µl of control sera containing different contents of bilirubin was spotted to the spreading layer of each 10 pieces of the above 4 kinds of the multilayer analytical elements, and incubated at 37° C. for 5 minutes. Then, the optical density of the color in each element was measured from the PET support side by reflection photometry, and the mean value of the optical densities and the reproducibility (coefficient of variation; CV) were calculated. The results are summarized in the following table.

|  | Bilirubin Concentration | | | |
|---|---|---|---|---|
|  | 1.6 | 4.3 | 11.0 | 17.2 |
|  | Mean Value of Optical Density | | | |
| Example 4 | 0.212 | 0.263 | 0.390 | 0.915 |
| Comparative 3A | 0.213 | 0.263 | 0.385 | 0.505 |
| Comparative 3B | 0.525 | 0.580 | 0.690 | 0.723 |
| Comparative 3C | 0.519 | 0.584 | 0.684 | 0.719 |
|  | Reproducibility (CV %) | | | |
| Example 4 | 3.2 | 1.8 | 1.6 | 1.9 |
| Comparative 3A | 4.1 | 3.9 | 4.2 | 5.2 |
| Comparative 3B | 3.5 | 2.8 | 6.3 | 7.2 |
| Comparative 3C | 3.6 | 3.1 | 4.9 | 5.4 |

The results of Properties Evaluation Test 3 indicate that the background color of the multilayer analytical element of the invention is little and the slope of calibration curve is great. Moreover, the reproducibility representing accuracy is small over the whole bilirubin concentration range compared to the elements of the prior art. Particularly, extremely small CV values in the bilirubin concentration range of 4.3 mg/dl to 17.2 mg/dl indicate that the measuring accuracy of the analytical element of the invention is excellent.

Properties Evaluation Test 4

The four kinds of the multilayer analytical elements were cut into strips 15 mm in width, and coiled around a core so that the fabric spreading layer was in contact with the core. They were allowed to stand at 35° C. for 7 days. Each strip was unwound, and the fouling state of the surface of each PET support was observed. The results were indicated in the following table.

|  | Fouling State |
|---|---|
| Example 4 | Fiber dust did not adhere |
| Comparative 3A | Fine fiber dust adhered all over the surface |
| Comparative 3B | " |
| Comparative 3C | Fiber dust did not adhere |

From the above results, since fiber dust did not adhere, the analytical element of the invention is excellent in the facility of handling during the manufacturing process as well as Comparative Example 3C.

In the sum of the results of the above evaluation tests, the spreading layer of the integral multilayer analytical element of the invention is bound to the water absorption layer with a suitable strength, and it can securely hold the diazonium salt without decomposing it. The background color is little. The reproducibility of the analytical results is good, and the element can measure in a high accuracy. Moreover, the release of fiber dust from the fabric spreading layer is not observed.

Example 5

A multilayer analytical element was prepared according to Example 2 of Japanese Patent KOKAI No. 60-14141.

A reagent layer was provided on a white PET film (support) 180 µm in thickness by coating the following aqueous solution so as to become the following amount, and dried.

| | |
|---|---|
| p-Sulfobenzenediazonium p-toluenesulfonate | 340 mg/m$^2$ |
| Dipylline | 12.5 g/m$^2$ |
| Sulfosalicylic acid | 1.0 g/m$^2$ |
| Octylphenoxypolyethoxyethanol (Containing 10 hydroxyethylene units on average) | 50 mg/m$^2$ |
| Carboxymethyl cellulose | 30 g/m$^2$ |

The reagent layer was uniformly moistened with water, and the roughed plain weave fabric obtained in Example 1 was lightly pressed to laminated thereon as the porous registration layer to obtain an integral multilayer analytical element for the quantitative analysis of bilirubin.

The analytical element was cut into rectangular pieces of 5 mm × 10 mm, and fixed to the tip of a PET holder of 5 mm × 70 mm by using a double face adhesive tape to complete an analytical device for the quantitative analysis of bilirubin. Each 10 µl of control sera containing different contents of bilirubin was spotted to the porous registration layer of 10 pieces of the analytical device, and incubated at 37° C. for 3 minutes. Then, the optical density of the color in the porous registration layer was measured from the porous registration layer side by reflection photometry, and the mean value of the optical densities and the reproducibility (coefficient of variation; CV) were calculated. As a result, the measuring accuracy is excellent, though it is slightly inferior to the results in Example 4, Properties Evaluation Test 3.

I claim:

1. In an integral multilayer analytical element comprising a reagent layer containing an indicator reagent composition capable of producing a detectable change corresponding to an analyte and a porous spreading layer composed of a fibrous fabric superposed on the reagent layer, the improvement which comprises said fabric being composed of fibers having a roughed surface formed by alkali etching, the fabric having an exposed and unexposed face, the fibers having a roughed surface comprising roughed portions being at least on the exposed face of the fabric, and wherein the depth of the roughness of the roughed surface in the direction perpendicular to the fiber axis is from 0.2 to 0.7 μm, and the roughed portions being further roughed with a fine roughness of a depth from about 50 nm to 200 nm, the density of the roughness of the roughed surface being from about 1 to 200/μm.

2. The analytical element of claim 1 wherein said yarn is filament yarn composed of long fibers and said fabric is woven fabric or knitted fabric.

3. The analytical element of claim 1 wherein said yarn is spun yarn, and said fabric is woven fabric or knitted fabric.

4. The analytical element of claim 1, claim 2 or claim 3 wherein said reagent layer is provided on a light-transmissive water-impermeable support.

5. The analytical element of claim 1, claim 2 or claim 3 wherein said reagent layer is provided on a light-reflective or opaque and water-impermeable support.

6. The analytical element of claim 5, wherein said reagent layer is provided on a light-transmissive water-impermeable support.

7. The analytical element of claim 5, wherein said reagent layer is provided on a light-reflective or opaque and water-impermeable support.

8. In an integral multilayer analytical element comprising a water-absorptive layer containing a hydrophilic polymer and a porous spreading layer composed of a fibrous fabric containing an indicator composition capable of producing a detectable change corresponding to an analyte superposed on the water-absorptive layer, the improvement which comprises said fabric being composed of fibers having a roughed surface formed by alkali etching, the fabric having an exposed and unexposed face, the fibers having a roughed surface comprising roughed portions being at least on the exposed face of the fabric, and wherein the depth of the roughness of the roughed surface in the direction perpendicular to the fiber axis is from 0.2 to 0.7 μm, and the roughed portions being further roughed with a fine roughness of a depth from about 50 nm to 200 nm, the density of the roughness of the roughed surface being from about 1 to 200/μm.

9. The analytical element of claim 8 wherein said yarn is filament yarn composed of long fibers and said fabric is woven fabric or knitted fabric.

10. The analytical element of claim 8 wherein said yarn is spun yarn, and said fabric is woven fabric or knitted fabric.

11. The analytical element of claim 1 or 8 wherein said reagent composition contains a diazonium salt or a tetrazolium salt.

12. The analytical element of claim 1 or 8 wherein the fibrous fabric is initially hydrophobic and is made hydrophilic by the alkali etching.

* * * * *